United States Patent
Solaun et al.

(10) Patent No.: US 12,402,886 B2
(45) Date of Patent: Sep. 2, 2025

(54) DETACHMENT INDICATOR FOR IMPLANT DEPLOYMENT

(71) Applicant: DePuy Synthes Products, Inc., Raynham, MA (US)

(72) Inventors: Daniel Solaun, Miami, FL (US); David Blumenstyk, Miami, FL (US); Masood Siddiqui, Raynham, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 17/847,913

(22) Filed: Jun. 23, 2022

(65) Prior Publication Data
US 2023/0414222 A1   Dec. 28, 2023

(51) Int. Cl.
A61B 17/12 (2006.01)
A61M 25/00 (2006.01)
A61M 25/01 (2006.01)

(52) U.S. Cl.
CPC .... *A61B 17/1214* (2013.01); *A61B 17/12113* (2013.01); *A61M 25/0147* (2013.01); *A61B 2017/12054* (2013.01); *A61M 2025/0008* (2013.01)

(58) Field of Classification Search
CPC ...... A61M 25/0147; A61M 2025/0008; A61B 2017/0046; A61B 2090/0811
See application file for complete search history.

(56) References Cited

U.S. PATENT DOCUMENTS

| | | | |
|---|---|---|---|
| 2,220,203 A * | 11/1940 | Branin | F16G 11/106 403/368 |
| 3,429,408 A | 2/1969 | Maker et al. | |
| 4,858,810 A * | 8/1989 | Intlekofer | A61B 17/3403 24/115 M |
| 5,108,407 A | 4/1992 | Geremia et al. | |
| 5,122,136 A | 6/1992 | Guglielmi et al. | |
| D329,698 S * | 9/1992 | Loney | D24/143 |
| 5,234,437 A | 8/1993 | Sepetka | |
| 5,250,071 A | 10/1993 | Palermo | |
| 5,263,964 A * | 11/1993 | Purdy | A61B 17/12022 128/899 |

(Continued)

FOREIGN PATENT DOCUMENTS

| | | |
|---|---|---|
| CN | 102125451 A | 7/2011 |
| CN | 103356260 A | 10/2013 |

(Continued)

*Primary Examiner* — Tan-Uyen T Ho
*Assistant Examiner* — Osama Nemer
(74) *Attorney, Agent, or Firm* — TROUTMAN PEPPER LOCKE LLP

(57) ABSTRACT

A delivery system for deploying an implantable medical device to a target location of a body vessel can include a tubular body with a lumen extending therethrough, a pull wire extending through the lumen, and a proximal support tube disposed within the lumen and engaged to the pull wire such that proximal translation of the support tube causes proximal translation of the pull wire. The proximal support tube can include a marked distal section that is not visible to an operator of the delivery system prior to the release of the implant and that becomes visible when the proximal support tube is pulled proximally a sufficient distance to cause the delivery system to release the implant.

20 Claims, 7 Drawing Sheets

(56) References Cited

U.S. PATENT DOCUMENTS

| | | |
|---|---|---|
| 5,334,210 A | 8/1994 | Gianturco |
| 5,350,397 A | 9/1994 | Palermo et al. |
| 5,382,259 A | 1/1995 | Phelps et al. |
| 5,392,791 A | 2/1995 | Nyman |
| 5,484,409 A | 1/1996 | Atkinson et al. |
| 5,536,248 A | 7/1996 | Weaver et al. |
| 5,569,221 A | 10/1996 | Houser et al. |
| 5,645,558 A | 7/1997 | Horton |
| 5,899,935 A | 5/1999 | Ding |
| 5,925,059 A | 7/1999 | Palermo et al. |
| 6,113,622 A | 9/2000 | Tieshima |
| 6,203,547 B1 | 3/2001 | Nguyen et al. |
| 6,391,037 B1 | 5/2002 | Greenhalgh |
| 6,454,780 B1 | 9/2002 | Wallace |
| 6,506,204 B2 | 1/2003 | Mazzocchi |
| 6,561,988 B1 | 5/2003 | Turturro et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,384,407 B2 | 6/2008 | Rodriguez et al. |
| 7,708,754 B2 | 5/2010 | Balgobin et al. |
| 7,708,755 B2 | 5/2010 | Davis, III et al. |
| 7,799,052 B2 | 9/2010 | Balgobin et al. |
| 7,811,305 B2 | 10/2010 | Balgobin et al. |
| 7,819,891 B2 | 10/2010 | Balgobin et al. |
| 7,819,892 B2 | 10/2010 | Balgobin et al. |
| 7,901,444 B2 | 3/2011 | Slazas |
| 7,985,238 B2 | 7/2011 | Balgobin et al. |
| 8,062,325 B2 | 11/2011 | Mitelberg et al. |
| 8,333,796 B2 | 12/2012 | Tompkins et al. |
| 8,926,650 B2 | 1/2015 | Que et al. |
| 8,956,381 B2 | 2/2015 | Que et al. |
| 9,155,540 B2 | 10/2015 | Lorenzo |
| 9,232,992 B2 | 1/2016 | Heidner |
| 9,314,326 B2 | 4/2016 | Wallace et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,120 B2 | 5/2017 | Agodzki et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,918,718 B2 | 3/2018 | Lorenzo |
| 10,149,676 B2 | 12/2018 | Mirigian et al. |
| 10,285,710 B2 | 5/2019 | Lorenzo et al. |
| 10,292,851 B2 | 5/2019 | Gorochow |
| 10,420,563 B2 | 9/2019 | Hebert et al. |
| 10,517,604 B2 | 12/2019 | Bowman et al. |
| 10,668,258 B1 | 6/2020 | Calhoun et al. |
| 10,806,402 B2 | 10/2020 | Cadieu et al. |
| 10,806,461 B2* | 10/2020 | Lorenzo ............ A61M 25/0054 |
| 11,951,026 B2 | 4/2024 | Clinger et al. |
| 2001/0049519 A1 | 12/2001 | Holman et al. |
| 2002/0072705 A1 | 6/2002 | Vrba et al. |
| 2002/0165569 A1 | 11/2002 | Ramzipoor et al. |
| 2002/0183786 A1 | 12/2002 | Girton |
| 2003/0009208 A1 | 1/2003 | Snyder et al. |
| 2003/0093094 A1 | 5/2003 | Diaz et al. |
| 2003/0181942 A1 | 9/2003 | Sutton et al. |
| 2004/0034363 A1 | 2/2004 | Wilson et al. |
| 2004/0059367 A1 | 3/2004 | Davis et al. |
| 2004/0087964 A1 | 5/2004 | Diaz et al. |
| 2006/0025801 A1 | 2/2006 | Lulo et al. |
| 2006/0064151 A1 | 3/2006 | Guterman |
| 2006/0100687 A1 | 5/2006 | Fahey et al. |
| 2006/0116711 A1 | 6/2006 | Elliott et al. |
| 2006/0116714 A1 | 6/2006 | Sepetka et al. |
| 2006/0135986 A1 | 6/2006 | Wallace et al. |
| 2006/0206139 A1 | 9/2006 | Tekulve |
| 2006/0241685 A1 | 10/2006 | Wilson et al. |
| 2006/0247677 A1 | 11/2006 | Cheng et al. |
| 2006/0276824 A1 | 12/2006 | Mitelberg et al. |
| 2006/0276825 A1 | 12/2006 | Mitelberg et al. |
| 2006/0276826 A1 | 12/2006 | Mitelberg et al. |
| 2006/0276827 A1 | 12/2006 | Mitelberg et al. |
| 2006/0276830 A1 | 12/2006 | Balgobin et al. |
| 2006/0276833 A1 | 12/2006 | Balgobin et al. |
| 2007/0010850 A1 | 1/2007 | Balgobin et al. |
| 2007/0055302 A1 | 3/2007 | Henry et al. |
| 2007/0083132 A1 | 4/2007 | Sharrow |
| 2007/0203519 A1 | 8/2007 | Lorenzo et al. |
| 2007/0233168 A1 | 10/2007 | Davis et al. |
| 2007/0270903 A1 | 11/2007 | Davis, III et al. |
| 2008/0027561 A1 | 1/2008 | Mitelberg et al. |
| 2008/0045997 A1 | 2/2008 | Balgobin et al. |
| 2008/0097462 A1 | 4/2008 | Mitelberg et al. |
| 2008/0119887 A1 | 5/2008 | Que et al. |
| 2008/0269719 A1 | 10/2008 | Balgobin et al. |
| 2008/0269721 A1 | 10/2008 | Balgobin et al. |
| 2008/0281350 A1 | 11/2008 | Sepetka |
| 2008/0300616 A1 | 12/2008 | Que et al. |
| 2008/0306503 A1 | 12/2008 | Que et al. |
| 2009/0062726 A1 | 3/2009 | Ford et al. |
| 2009/0099592 A1 | 4/2009 | Buiser et al. |
| 2009/0270877 A1 | 10/2009 | Johnson et al. |
| 2009/0312748 A1* | 12/2009 | Johnson ............ A61B 17/12022 606/1 |
| 2010/0094395 A1* | 4/2010 | Kellett ............... A61B 17/1215 623/1.11 |
| 2010/0114017 A1 | 5/2010 | Lenker et al. |
| 2010/0206453 A1 | 8/2010 | Leeflang et al. |
| 2010/0324649 A1 | 12/2010 | Mattsson |
| 2011/0092997 A1 | 4/2011 | Kang |
| 2011/0118772 A1 | 5/2011 | Chen et al. |
| 2011/0118776 A1* | 5/2011 | Chen ............... A61B 17/12022 606/200 |

(56) References Cited

U.S. PATENT DOCUMENTS

| | | |
|---|---|---|
| 2011/0202085 A1 | 8/2011 | Loganathan et al. |
| 2011/0295303 A1 | 12/2011 | Freudenthal |
| 2012/0035707 A1 | 2/2012 | Mitelberg et al. |
| 2012/0041472 A1 | 2/2012 | Tan et al. |
| 2012/0083868 A1 | 4/2012 | Shrivastava et al. |
| 2012/0172913 A1 | 7/2012 | Kurrus et al. |
| 2012/0172921 A1 | 7/2012 | Yamanaka et al. |
| 2012/0179194 A1 | 7/2012 | Wilson et al. |
| 2012/0283768 A1 | 11/2012 | Cox et al. |
| 2012/0289772 A1 | 11/2012 | O'Connell et al. |
| 2013/0066413 A1 | 3/2013 | Jin et al. |
| 2013/0296915 A1 | 11/2013 | Bodewadt |
| 2013/0325054 A1 | 12/2013 | Watson |
| 2013/0338678 A1* | 12/2013 | Loushin ................ A61F 11/202 |
| | | 606/109 |
| 2014/0058435 A1 | 2/2014 | Jones et al. |
| 2014/0088565 A1 | 3/2014 | Vongphakdy et al. |
| 2014/0135812 A1 | 5/2014 | Divino et al. |
| 2014/0200607 A1 | 7/2014 | Sepetka et al. |
| 2014/0207175 A1 | 7/2014 | Aggerholm |
| 2014/0243883 A1* | 8/2014 | Tsukashima ....... A61B 17/1214 |
| | | 606/200 |
| 2014/0277078 A1 | 9/2014 | Slazas et al. |
| 2014/0277084 A1 | 9/2014 | Mirigian et al. |
| 2014/0277085 A1 | 9/2014 | Mirigian et al. |
| 2014/0277092 A1 | 9/2014 | Teoh et al. |
| 2014/0277093 A1 | 9/2014 | Guo et al. |
| 2014/0277100 A1 | 9/2014 | Kang |
| 2015/0005808 A1 | 1/2015 | Chouinard et al. |
| 2015/0025562 A1 | 1/2015 | Dinh et al. |
| 2015/0119884 A1* | 4/2015 | Fung ................ A61B 18/1492 |
| | | 606/41 |
| 2015/0164666 A1 | 6/2015 | Johnson et al. |
| 2015/0182227 A1 | 7/2015 | Le et al. |
| 2015/0230802 A1 | 8/2015 | Lagodzki et al. |
| 2015/0335333 A1 | 11/2015 | Jones et al. |
| 2016/0008003 A1 | 1/2016 | Kleshinski et al. |
| 2016/0022275 A1 | 1/2016 | Garza |
| 2016/0022445 A1 | 1/2016 | Ruvalcaba et al. |
| 2016/0045347 A1 | 2/2016 | Smouse et al. |
| 2016/0157869 A1 | 6/2016 | Elgård et al. |
| 2016/0228125 A1 | 8/2016 | Pederson, Jr. et al. |
| 2016/0278782 A1 | 9/2016 | Anderson et al. |
| 2016/0310304 A1 | 10/2016 | Mialhe |
| 2016/0331383 A1 | 11/2016 | Hebert et al. |
| 2016/0346508 A1 | 12/2016 | Williams et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072165 A1 | 3/2017 | Lim et al. |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095258 A1 | 4/2017 | Tassoni et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105739 A1* | 4/2017 | Dias ...................... A61B 90/39 |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0245864 A1 | 8/2017 | Franano et al. |
| 2017/0245885 A1 | 8/2017 | Lenker |
| 2017/0252064 A1 | 9/2017 | Staunton |
| 2017/0258476 A1 | 9/2017 | Hayakawa et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2017/0367712 A1 | 12/2017 | Johnson et al. |
| 2018/0028779 A1 | 2/2018 | von Oepen et al. |
| 2018/0036508 A1 | 2/2018 | Ozasa et al. |
| 2018/0078263 A1* | 3/2018 | Stoppenhagen . A61B 17/12113 |
| 2018/0228493 A1 | 8/2018 | Aguilar et al. |
| 2018/0250150 A1 | 9/2018 | Majercak et al. |
| 2018/0280667 A1 | 10/2018 | Keren |
| 2018/0289375 A1 | 10/2018 | Hebert et al. |
| 2018/0296222 A1 | 10/2018 | Hebert et al. |
| 2018/0325706 A1 | 11/2018 | Hebert et al. |
| 2019/0142565 A1 | 5/2019 | Follmer et al. |
| 2019/0159784 A1 | 5/2019 | Sananes et al. |
| 2019/0192162 A1 | 6/2019 | Lorenzo et al. |
| 2019/0201688 A1 | 7/2019 | Olson |
| 2019/0231566 A1* | 8/2019 | Tassoni ............ A61B 17/12022 |
| 2019/0255290 A1 | 8/2019 | Snyder et al. |
| 2019/0314033 A1 | 10/2019 | Mirigian et al. |
| 2019/0328398 A1 | 10/2019 | Lorenzo |
| 2020/0015876 A1 | 1/2020 | Chou et al. |
| 2020/0078024 A1 | 3/2020 | Tekulve |
| 2020/0138448 A1 | 5/2020 | Dasnurkar et al. |
| 2020/0147347 A1 | 5/2020 | Cottone |
| 2020/0187951 A1 | 6/2020 | Blumenstyk |
| 2020/0229957 A1 | 7/2020 | Bardsley et al. |
| 2020/0397444 A1 | 12/2020 | Montidoro et al. |
| 2020/0406048 A1 | 12/2020 | Rentas Torres et al. |
| 2021/0001082 A1 | 1/2021 | Lorenzo et al. |

(56) References Cited

U.S. PATENT DOCUMENTS

| | | |
|---|---|---|
| 2021/0045759 A1 | 2/2021 | Merhi et al. |
| 2021/0085498 A1 | 3/2021 | Nygaard et al. |
| 2021/0186513 A1 | 6/2021 | Hoshino et al. |
| 2021/0196281 A1 | 7/2021 | Blumenstyk et al. |
| 2021/0213252 A1 | 7/2021 | Lorenzo et al. |
| 2021/0338248 A1 | 11/2021 | Lorenzo et al. |
| 2021/0346002 A1 | 11/2021 | Lorenzo et al. |
| 2021/0353299 A1 | 11/2021 | Hamel et al. |
| 2023/0200819 A1 | 6/2023 | Blumenstyk et al. |

FOREIGN PATENT DOCUMENTS

| | | | |
|---|---|---|---|
| CN | 104203341 A | 12/2014 | |
| CN | 106456422 A | 2/2017 | |
| CN | 109770985 A | 5/2019 | |
| EP | 1985244 A2 | 10/2008 | |
| EP | 2498691 | 9/2012 | |
| EP | 3092956 A1 | 11/2016 | |
| EP | 3501427 A1 | 6/2019 | |
| EP | 3795097 A1 | 3/2021 | |
| EP | 3799803 A1 | 4/2021 | |
| EP | 3854321 A1 | 7/2021 | |
| EP | 1188414 A1 | 3/2022 | |
| EP | 4119065 A1 | 1/2023 | |
| JP | H10-507090 A | 7/1998 | |
| JP | 2006-334408 A | 12/2006 | |
| JP | 2006346350 A | 12/2006 | |
| JP | 2012-523943 A | 10/2012 | |
| JP | 2013-78584 A | 5/2013 | |
| JP | 2014-399 A | 1/2014 | |
| JP | 2016-179174 A | 10/2016 | |
| JP | 2017-529894 A | 10/2017 | |
| WO | WO-2007070793 A2 * | 6/2007 | ............... A61F 2/95 |
| WO | 2008064209 A1 | 5/2008 | |
| WO | WO 2009/132045 A2 | 10/2009 | |
| WO | WO 2012/158152 A1 | 11/2012 | |
| WO | WO-2016014985 A1 * | 1/2016 | ............ A61B 17/12 |
| WO | WO 2017/066386 A1 | 4/2017 | |
| WO | WO 2018/022186 A1 | 2/2018 | |
| WO | WO 2020/148768 A1 | 7/2020 | |

\* cited by examiner

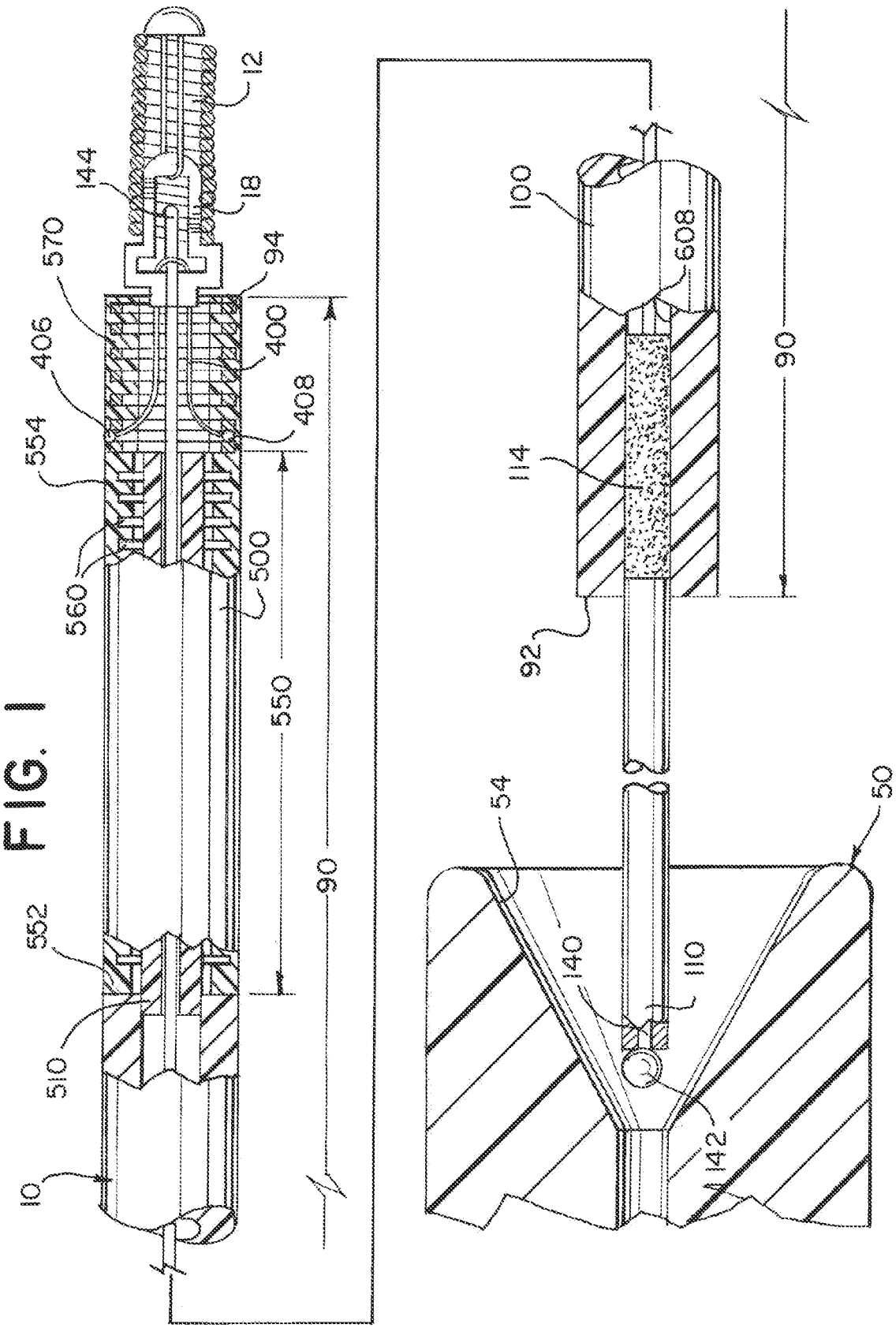

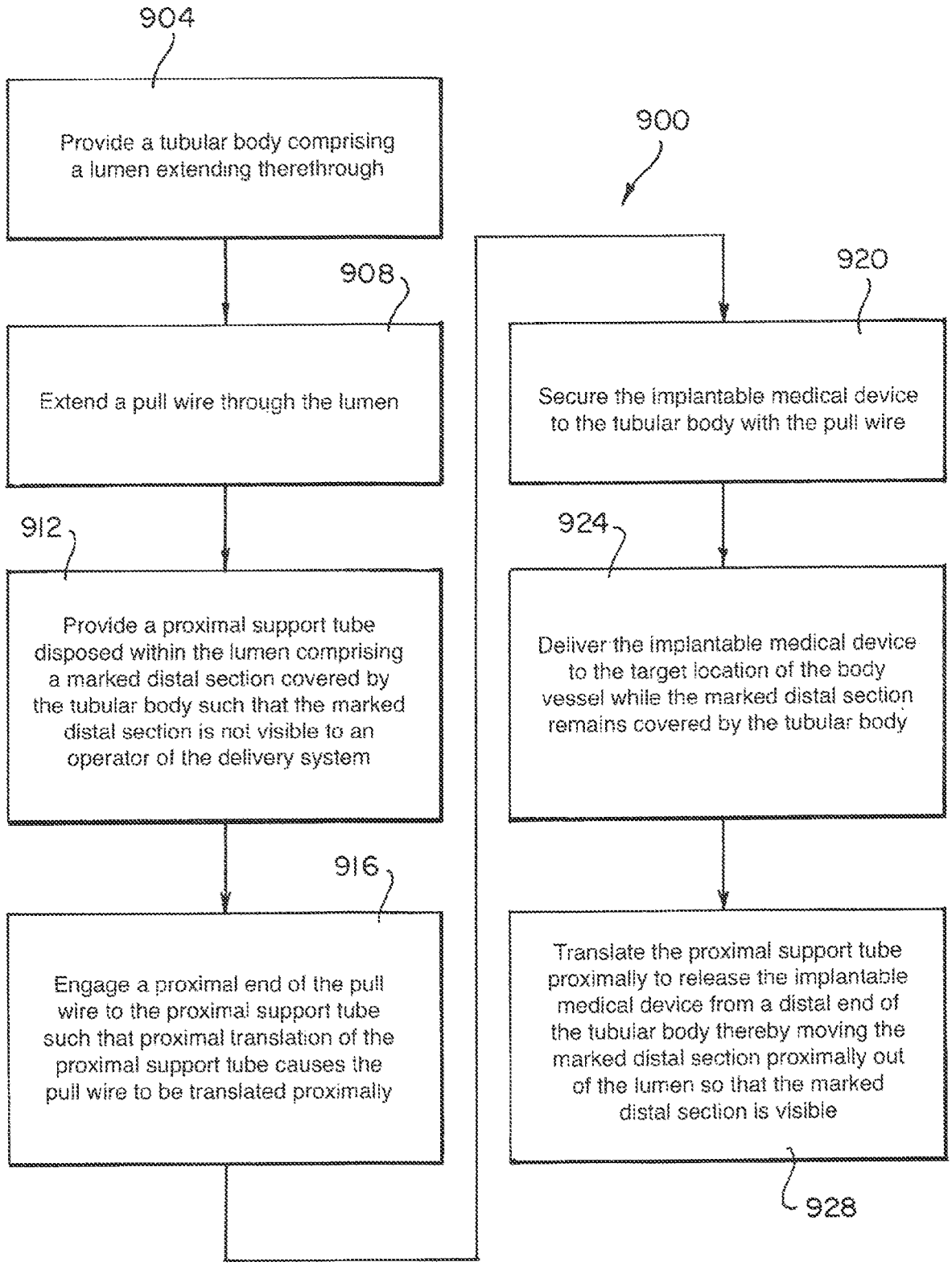

DETACHMENT INDICATOR FOR IMPLANT DEPLOYMENT

FIELD OF INVENTION

The present invention relate to aneurysm treatment devices and more particularly, to a delivery system for deploying an implantable medical device to a target location of a body vessel that includes a detachment indicator indicating when the implantable medical device has been deployed.

BACKGROUND

Numerous intravascular implant devices are known in the field. Many are deployed mechanically, via systems that combine one or more catheters and wires for delivery.

Examples of implants that can be delivered mechanically include embolic elements, stents, grafts, drug delivery implants, flow diverters, filters, stimulation leads, sensing leads, or other implantable structures delivered through a microcatheter. A physician desires feedback that a detachment cycle has been completed correctly. In most mechanical delivery systems, an inner tube is held within a lumen of a delivery system pusher and is attached to an internal wire that travels the length of the device. When pulled, the internal wire translates backwards to detach the implant. In traditional systems, an identifier that the detachment cycle has been completed is that the inner tube has been translated and thus increases in length. However, in traditional deployment systems, it is difficult for the physician to visually determine whether the implant has been deployed successfully because the small change in length is difficult to determine visually.

Accordingly, there is a need for a deployment system that has a detachment indicator indicating to the physician that the implant has been successfully deployed.

SUMMARY

Disclosed herein are various exemplary systems, devices, and methods of the present disclosure that can address the above needs. Examples can generally include a delivery system for deploying an implantable medical device to a target location of a body vessel. The delivery system can include a tubular body that includes a lumen extending therethrough. The delivery system can include a pull wire that extends through the lumen. The delivery system can include a proximal support tube that is disposed within the lumen. The proximal support tube can include a marked distal section that is covered by the tubular body such that the marked distal section is not visible to an operator of the delivery system. The proximal support tube can be configured to engage a proximal end of the pull wire such that proximal translation of the proximal support tube causes the pull wire to be translated proximally thereby releasing an implantable medical device from a distal end of the tubular body. The proximal support tube can be configured such that proximal translation of the proximal support tube resulting in release of the implantable medical device moves the marked distal section from the lumen of the tubular body so that the marked distal section is visible.

The delivery system can further include a loop wire that includes a loop opening at a distal portion of the loop wire positioned approximate the distal end of the tubular body. The loop wire and the pull wire are positioned to secure the implantable medical device to the delivery system.

The implantable medical device can be deployed in response to proximal translation of the proximal support tube, which can cause a distal end of the pull wire to exit the loop opening, which can cause the loop wire and the pull wire to disengage the medical device from the delivery system.

The marked distal section can include a laser etching visible to the operator of the delivery system upon deployment of the implantable medical device.

The marked distal section can include an anodized portion of the proximal support tube visible to an operator of the delivery system upon deployment of the implantable medical device.

The marked distal section can include a printed or dipped portion of the proximal support tube visible to an operator of the delivery system upon deployment of the implantable medical device.

The marked distal section can be visibly distinguishable from a remainder of the proximal support tube.

A remainder of the proximal support tube can include a first color, and the marked distal section can include a second color distinguishable from the first color.

Proximal translation of the proximal support tube can be between approximately 6 millimeters and approximately 12 millimeters to expose the marked distal portion.

Proximal translation of the proximal support tube can be between approximately 6 millimeters and approximately 12 millimeters to deploy the implantable medical device.

The tubular body can include a proximal tube, a flexible tube distal to the proximal tube, and a distal tube distal to the flexible tube.

The flexible tube can include interference cuts.

The distal tube can further include a compressed distal portion positioned approximate the implantable medical device. The compressed portion can provide an elastic force against the implantable medical device to thereby facilitate the release of the implantable medical device from the delivery system.

The compressed distal portion can include a spiral cut portion of the distal tube.

In another aspect, a method for using a delivery system to deploy an implantable medical device to a target location of a body vessel is disclosed. The method can include providing a tubular body. The tubular body can include a lumen extending therethrough. The method can include extending a pull wire through the lumen. The method can include providing a proximal support tube that is disposed within the lumen. The proximal support tube can include a marked distal section that is covered by the tubular body such that the marked distal section is not visible to an operator of the delivery system. The method can include engaging a proximal end of the pull wire to the proximal support tube such that proximal translation of the proximal support tube causes the pull wire to be translated proximally. The method can include securing the implantable medical device to the tubular body with the pull wire. The method can include delivering the implantable medical device to the target location of the body vessel while the marked distal section remains covered by the tubular body. The method can include translating a proximal support tube proximally to release the implantable medical device from a distal end of the tubular body, thereby moving the marked distal section proximally out of the lumen so that the marked distal section is visible.

The marked distal section can include a laser etching visible to an operator of the delivery system upon deployment of the implantable medical device.

The marked distal section can include an anodized portion of the proximal support tube visible to an operator of the delivery system upon deployment of the implantable medical device.

The marked distal section can include a printed or dipped portion of the proximal support tube visible to an operator of the delivery system upon deployment of the implantable medical device.

A remainder of the proximal support tube can include a first color and the marked distal section can include a second color distinguishable from the first color.

Proximal translation of the proximal support tube of between approximately 6 millimeters and approximately 12 millimeters exposes the marked distal portion and is effective to deploy the implantable medical device.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 1 is an illustration of a delivery system and implant, according to aspects of the present invention.

FIG. 9 is a flowchart of an exemplary method of using the deployment handle and delivery system to deploy an implant.

DETAILED DESCRIPTION

Figure 2A:
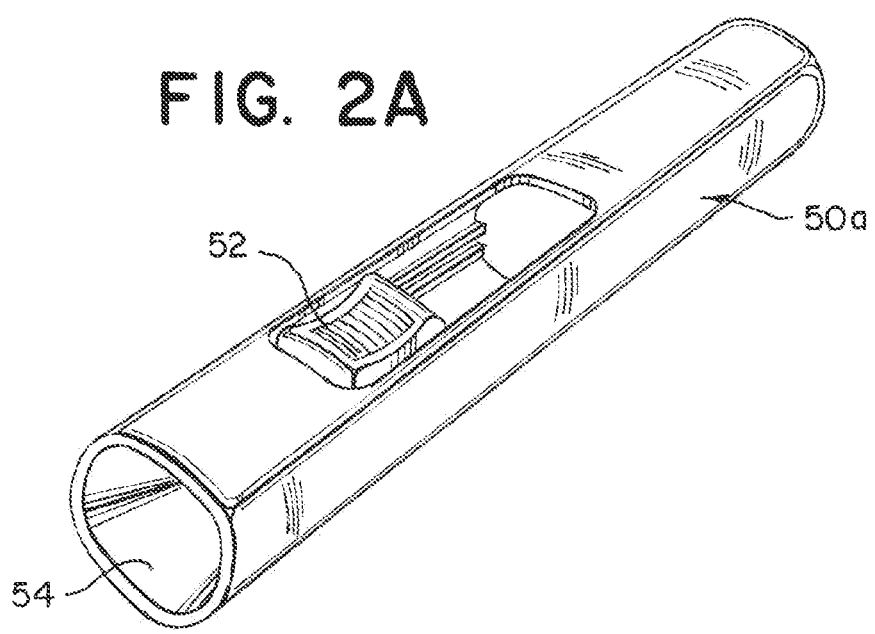
FIG. 2A-2C illustrate a deployment handle and delivery system in an unconnected state.

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the pertinent art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the pertinent art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Turning to the figures, FIG. 1 shows an example delivery system 10 for deploying an implantable medical device 12 to a target location of a body vessel. The example delivery system 10 can include a proximal tube 100, a flexible tube 550 positioned distal to the proximal tube 100, and a distal tube 570 positioned distal to the flexible tube 550. Flexible tube 550 has proximal end 552 and distal end 554. The proximal tube 100, flexible tube 550, and distal tube 570 may collectively have a lumen 608 extending therethrough. That is, lumen 608 extends from a proximal end of proximal tube 100, through flexible tube 550, and through distal tube 570. Collectively, proximal tube 100, flexible tube 550 and distal tube 570 can be referred to as a tubular body 90. The tubular body can include a proximal end 92 and a distal end 94, as shown in FIG. 1. Implant 12 can be positioned distal to the distal tube 570.

The flexible tube 550 can include a coiled wire, support coil that is attached at each end to the proximal tube 110 and the distal tube 570 respectively. Alternatively, the flexible tube 550 can include a laser cut hypotube including interference cuts 560 as illustrated in FIG. 1. In this example, the flexible tube 550 is preferably contiguous with the proximal tube 100 and the distal tube 570 such that the tubes 100, 550, 570 are formed from a single hypotube. The interference cuts 560 can provide a high level of flexibility to flexible tube 550. A sleeve 500 can surround the flexible tube 550 to provide a smooth outer surface of the delivery system 10 over the flexible tube 550.

An inner support tube 510 can be positioned within the lumen 608 of the flexible tube 550. The inner support tube 510 can be welded or otherwise attached to the inner sidewall of flexible tube 550. Inner support tube 510 can provide structural support to the flexible tube 550. In some examples, the inner support tube 510 can prevent the flexible tube 550 from elongating. The inner support tube 510 is optional if the interference cuts are made to allow the flexible tube 550 to have sufficient structural support in the absence of the support tube 510, or if other features are included to provide structural support to the flexible tube 550.

A pull wire 140 can extend through the lumen 608 of delivery system 10. Within lumen 608 of proximal tube 100 can be positioned a proximal support tube 110. Proximal support tube 110 can be welded or otherwise attached to the inner sidewall of proximal tube 100. Both proximal support tube 110 and inner support tube 510 can be considered as part of tubular body 90. Proximal support tube 110 can be considered to be located on proximal end 92 of the tubular body 90. The pull wire 140 can include a pull wire bead 142 located on a proximal end of pull wire 140. The pull wire bead 142 can be sized such that the pull wire bead 142 is larger than the space between the proximal support tube 110 such that the pull wire bead 142 interferes with the proximal support tube 110 and proximal support tube 110 retains the pull wire bead 142 proximal to the proximal tube 100. Alternatively, the proximal end of the pull wire can be welded to the proximal tube 110 or otherwise engaged to the proximal tube 110 as understood by a person skilled in the pertinent art.

A loop wire opening 405 of loop wire 400 (also illustrated with respect to FIGS. 8A-8D) can be located at a distal portion 404 of loop wire 400 and can extend through a locking member 18 of implant 12. The distal end 144 of pull wire 140 can be positioned through the loop wire opening 405 of loop wire 400 to secure implant 12 to the delivery system 10. Loop wire proximal ends 406, 408 can be attached to the distal tube 570 as illustrated. Additionally or alternatively, one or both of the loop wire proximal ends 406, 408 can be affixed to the proximal tube 100 to provide structural support to the flexible tube 550. Additionally, or alternatively, the loop wire proximal ends 406, 408 can be attached to the pull wire 140. In this example, the loop wire 400 can be made of an elastic material, such that proximal translation of the pull wire 140 can cause the loop wire 400 to stretch and become tensioned, which provides a resistant force against further proximal translation of pull wire 140. The loop wire 400 can be effective to prevent premature detachment of implant 12 from delivery system 10.

The proximal support tube 110 can include a marked distal section 114 that is located within the proximal tube 100. The marked distal section 114 can be configured to be hidden from view of an operator of the delivery system 10 while implant 12 is delivered to a target location within a patient. When the pull wire 140 is pulled proximally a distance sufficient to detach implant 12, the proximal support tube 110 can be configured to translate proximally, thereby causing the marked distal section 114 to exit the proximal tube 100 and become visible to an operator of the delivery system 10.

When the delivery system 10 is assembled, the flexible tube 550 and sleeve 500 can be more flexible than the distal tube 570 and the proximal tube 100. One way to measure flexibility is to perform a three-point bend test wherein a portion of the delivery system 10 is held fixed at two end points, a force is applied perpendicularly to the delivery system 10 centrally between the points, and flexibility is quantified by the length of deflection of the delivery system 10 caused by the force. When measured in this way, in some examples, the flexible tube 550 and sleeve 500 can be about 1.5 times more flexible than the distal tube 570 and about 20 times more flexible than the proximal tube 100. That is, when the three-point test is performed identically on the three sections 100, 550, and 570, the flexible tube 550 can deflect over a length that is about 1.5 times the deflection of the distal tube 570 and about 20 times the length of deflection of the proximal tube 100. Flexibility can be measured in other ways as would be appreciated and understood by a person having pertinent skill in the art.

According to some embodiments, the distal tube 570 can include a compressible distal portion 300 (as shown in greater detail in FIGS. 8A through 8D), which can be compressed and formed from a spiral-cut portion of the distal tube 570, formed by a laser cutting operation. Additionally, or alternatively, the compressible distal portion 300 can be formed of a wound wire, spiral ribbon, or other arrangement allowing axial adjustment according to the present invention. Preferably, compressible distal portion 300 is in the elongated condition at rest and automatically or resiliently returns to the elongated condition from a compressed condition, unless otherwise constrained. In some embodiments, the loop wire 400 is effective to hold the compressed distal portion 300 in compression while the implant 12 is delivered to the treatment site. Alternatively, the distal tube 570 can lack the compressible spring structure 300.

Pull wire 140 can be constructed out of any suitable material, for example, pull wire 140 can be constructed of stainless steel or memory shape material, such as nitinol. According to some embodiments, pull wire 140 can additionally be coated with polytetrafluoroethylene (PTFE).

Figure 2B:
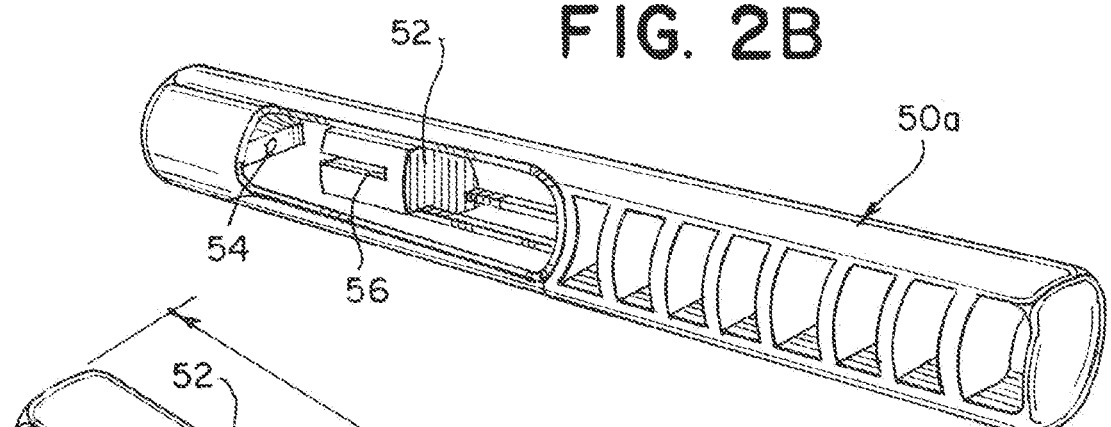
Figure 2C:
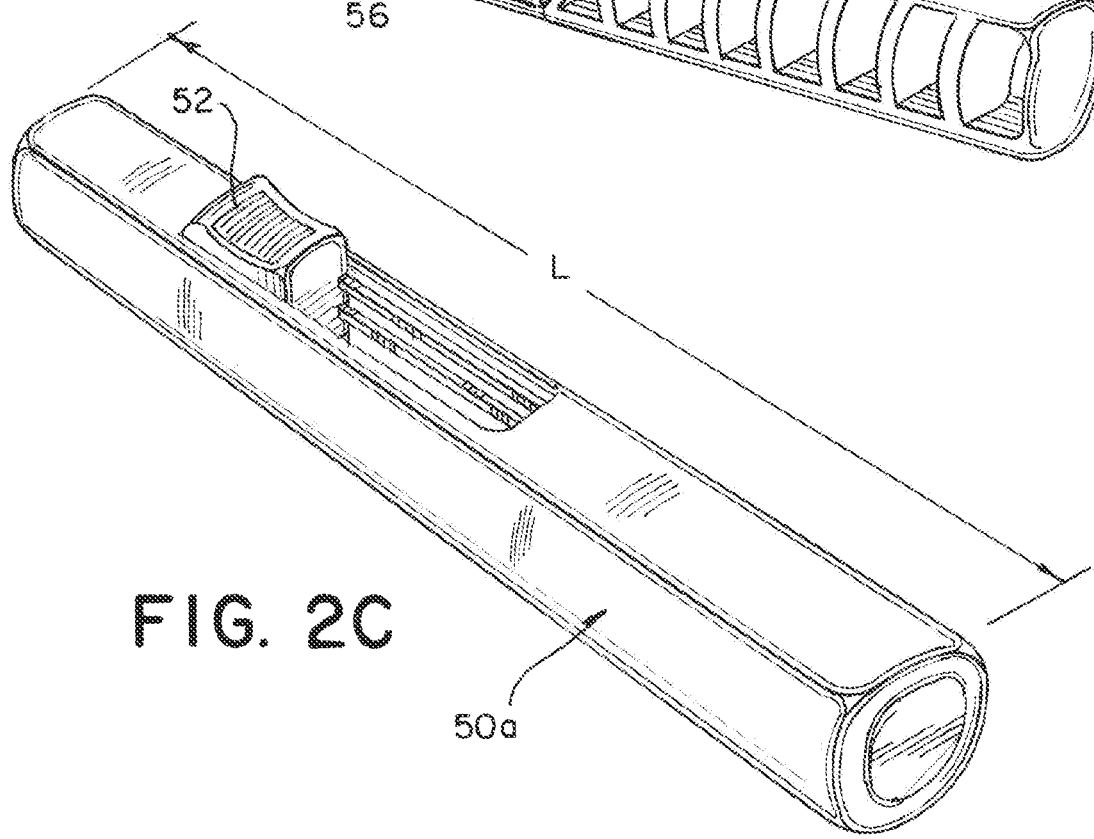

FIGS. 2A through 2C are illustration of an exemplary handle member 50, according to aspects of the present disclosure. A deployment handle 50 can include components as described in pending U.S. application Ser. No. 17/564,764, published as U.S. Patent Application Publication No. US 2023/0200819 A1 on Jun. 29, 2023, which is herein incorporated by reference as if included in its entirety. Numerous types of handle members can be used to retract the support tube 110 and pull wire 140 as understood by a person skilled in the pertinent art.

FIG. 2A is a top view perspective illustration of handle member 50 from the distal end, FIG. 2B is a bottom cut-away view of handle member 50 from the proximal end, and FIG. 2C is a top view perspective illustration of handle member 50 from the proximal end. The exemplary handle member 50 can include a handle button 52, an aperture 54, and a handle channel 56. The handle member may have a length L extending from a proximal end of the handle member 50 to the distal end of the handle member 50. According to some aspects of the present disclosure, the length L of handle member 50 can be approximately between 10 cm and 20 cm.

The handle channel 56, found on the bottom of handle member 50a, can be configured to engage with proximal support tube 110 and can have a length sufficient to engage to the length of proximal support tube 110. Aperture 54 has a diameter sufficient to fit proximal support tube 110 therethrough. Proximal support tube 110 is configured to pass through aperture 54 when engaging to handle member 50 at handle channel 56.

Handle button 52 can be configured to be pressed by an operator of the delivery system 10. When handle button 52 is pressed (e.g., towards a bottom surface of handle member 50), the proximal support tube 110 can be pressed against the top surface of handle channel 56, which can cause the support tube 110 and pull wire 140 to be retracted, thereby deploying the implant 12. When the proximal end of the delivery system 10 is removed from the handle 50, the marked distal section 114 of the support tube 110 can be visible to the operator. The marked distal section 114 provides a visible indication to the operator that the delivery system 10 has been properly manipulated to deploy the implant 12.

FIGS. 3-6 illustrate use of the delivery system 10 with another example handle 50. The operator can slide handle button 52 proximally to thereby detach the implant from the deployment system 10 and expose the marked distal section 114 of the proximal support tube 110 to provide a visual indication to the operator that the implant 12 has been successfully detached from the deployment system 10 and deployed in the target location of a patient's vasculature.

Figure 3:
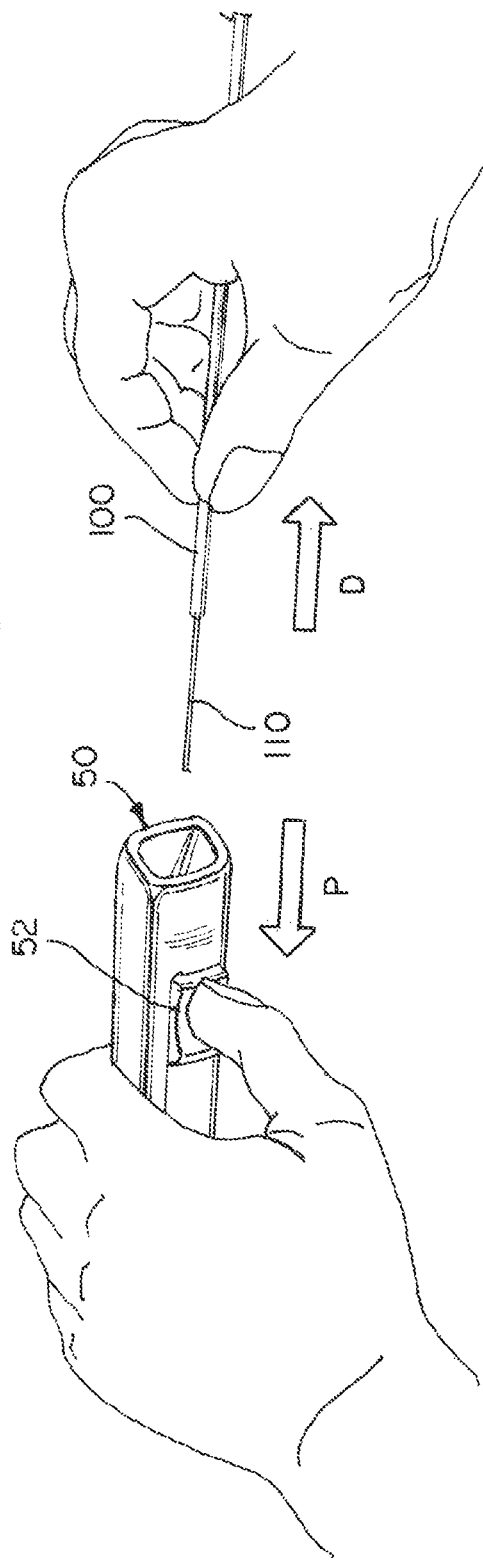
FIG. 3 illustrates a deployment handle and delivery system in an unconnected state.

FIG. 3 illustrates a deployment handle 50 and delivery system 10 in an unconnected state with the handle 50. The proximal direction (P) and distal direction (D) are indicated in the illustration. The proximal tube 100 can have a proximal support tube 110 extending in a proximal direction (P) therefrom. The proximal support tube 110 can be configured to be inserted into aperture 54 of handle member 50. As shown, handle member 50 can include a handle button 52, which allows the operator of the delivery system 10 and the handle member 50 to engage the proximal support tube 110 against the handle channel 56 such that the proximal support tube 110 can be translated proximally by the operator slide handle button 52 in a proximal direction (P) while handle button 52 is depressed. Proximal translation of the proximal support tube 110 can cause the pull wire 140 to be translated proximally to thereby release the implant 12 from the delivery system 10. As shown in FIG. 3, the marked distal section 114 of the proximal support tube 110 is not visible, because the implant 12 has not yet been deployed from the delivery system 10.

Figure 4:
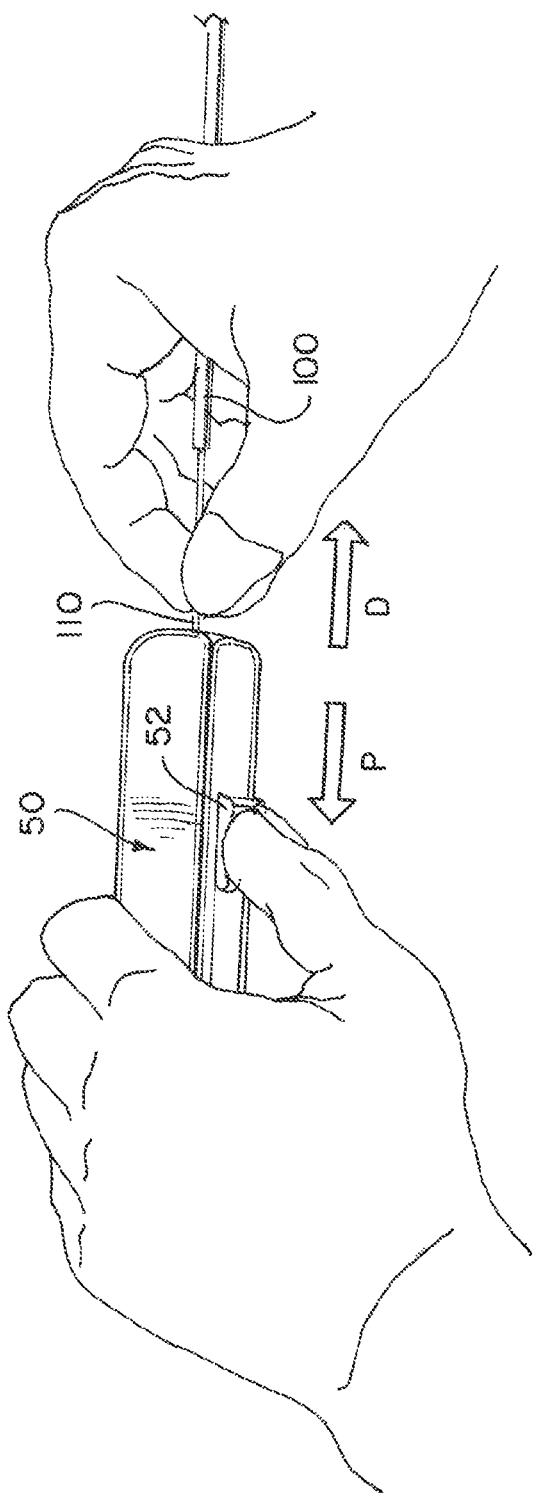
FIG. 4 illustrates a deployment handle and delivery system in a connected state.

FIG. 4 illustrates a deployment handle and delivery system in a connected state. As shown, an operator of the handle 50 and delivery system 10 can connect the proximal support tube 110 that extends from the proximal tube 100 by inserting the proximal support tube 110 into the aperture 54 of handle member 50. Proximal support tube 110 can be inserted into aperture 54 of handle member 50 until the proximal support tube 110 extends fully through a handle channel similar to handle channel 56, as described with respect to FIGS. 2A through 2C.

Figure 5:
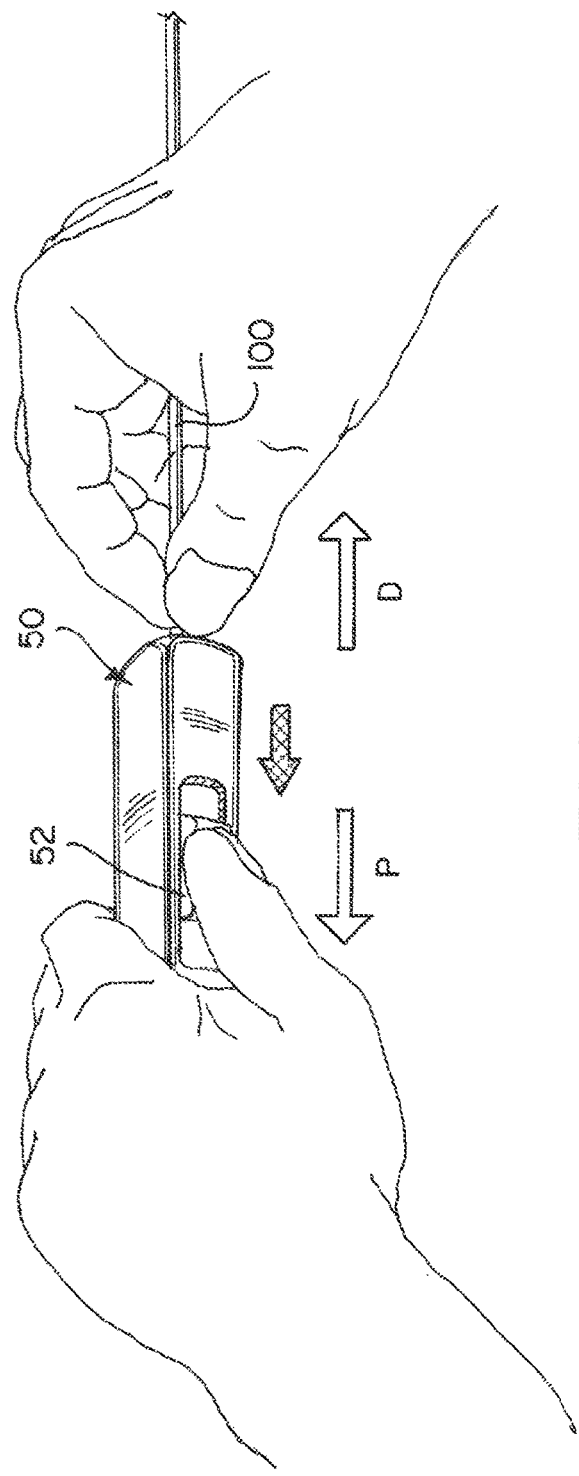
FIG. 5 illustrates a deployment handle and delivery system as the deployment handle is used to deploy an implant from the delivery system.

FIG. 5 illustrates a deployment handle and delivery system as the deployment handle is used to deploy an implant 12 from the delivery system 10. After the proximal support tube 110 is inserted through aperture 54 and fully extended into handle channel 56, the operator can slide the handle button 52 proximally. As handle button 52 is slid proximally, the proximal support tube 110 can slide proximally. As proximal support tube 110 slides proximally, the pull wire 140 can be proximally translated with the proximal translation of the proximal support tube 110. The proximal translation of pull wire 140 can deploy the implant 12 from delivery system 10. In some examples, a proximal shift of between approximately 6 mm and approximately 12 mm can be effective to deploy the implant 12 from the delivery system 10. In some examples, movement of handle button 52 proximally by between approximately 6 mm and approximately 12 mm may cause the proximal support tube 110 and the pull wire 140 to translate proximally by between approximately 6 mm and approximately 12 mm, which can cause the implant 12 to be deployed from delivery system 10.

Alternatively, the handle 50 may include a shuttle system to move the proximal support tube 110 a greater distance than the distance through which the handle button 52 travels.

Figure 6:
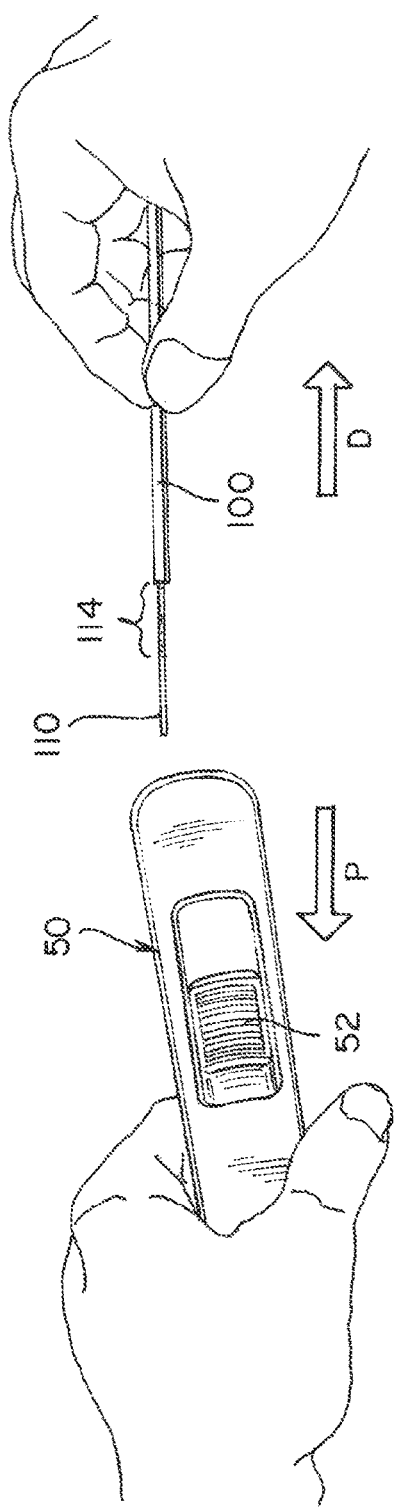
FIG. 6 shows a deployment handle and delivery system in an unconnected state after the implant is deployed.

FIG. 6 shows a deployment handle and delivery system in an unconnected state after the implant 12 is deployed. After the proximal support tube 110 and pull wire 140 are translated proximally to deploy implant 12 from delivery system 10, the marked distal section 114 can be exposed to an operator of the handle 50 and delivery system 10. In some examples, the marked distal section 114 can be created by laser etching a distal portion of the proximal support tube 110 in order to create the marked distal section 114 that is visually distinct from the remainder of the proximal support tube 110. In some examples, the marked distal section 114 can be created by an anodizing process that is applied to a distal portion of the proximal support tube 110 in order to create the marked distal section 114 that is visually distinct from the remainder of the proximal support tube 110. In some examples, the marked distal section 114 can be created by applying a color printing process to a distal portion of the proximal support tube 110 in order to create the marked distal section 114 that is visually distinct from the remainder of the proximal support tube 110. In some examples, the marked distal section 114 can be created by dipping a distal portion of the proximal support tube 110 in a respective paint color in order to create the marked distal section 114 that is visually distinct from the remainder of the proximal support tube 110. In some examples, the marked distal section 114 can be a first color, while the remainder of the proximal support tube can be a second color that is visually distinct from the first color.

Figure 7:
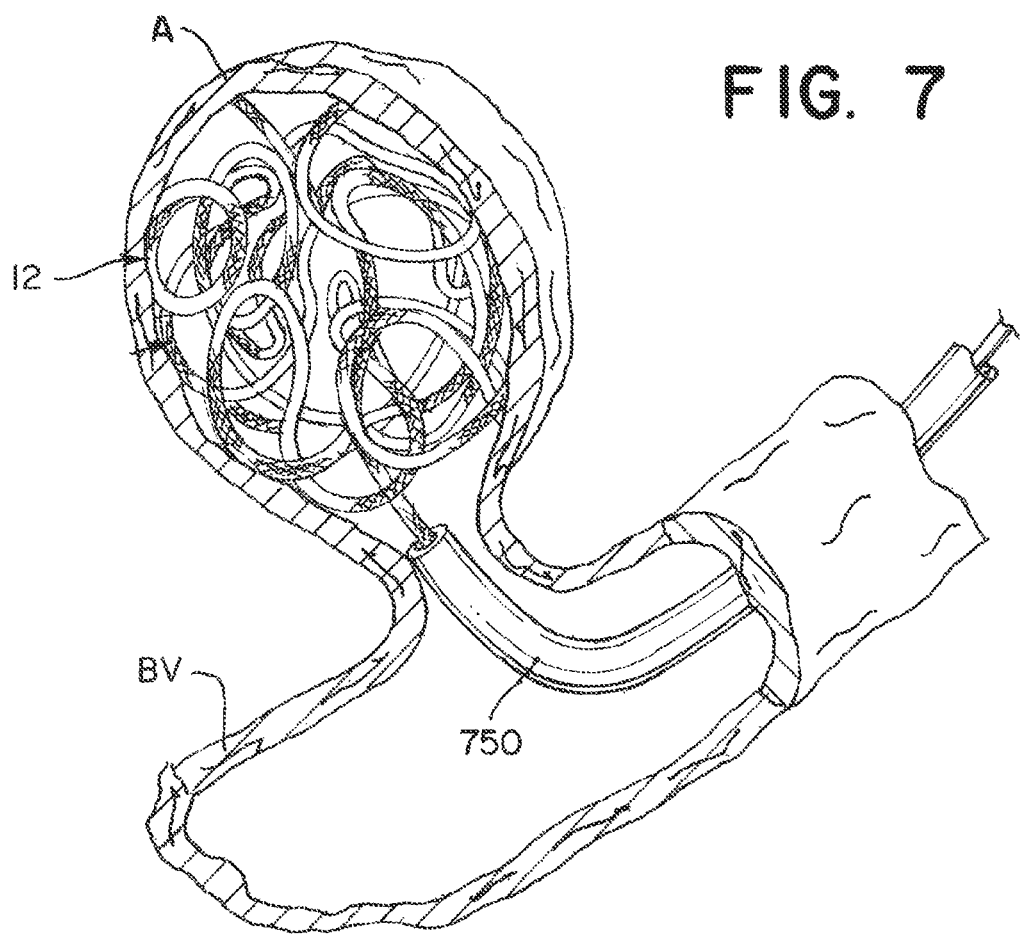
FIG. 7 is an illustration of embolic coils being positioned within an aneurysm according to aspects of the present invention.

FIG. 7 is an illustration of embolic implant 12 being delivered through catheter 750 and positioned within an aneurysm A on a blood vessel BV. The implant 12 can loop and bend with the aneurysm sac to form a thrombotic mass. The implant can loop back on themselves and/or loop next to other implants. As the aneurysm A becomes increasingly packed, overlapping portions of the implant 12 can press into each other. As illustrated, the implant 12 includes an embolic coil. Numerous types of implants can be deployed by a pull wire mechanism as understood by a person skilled in the pertinent art. For instance, implants can include an embolic braid, a stent, or flow diverter structure.

Figure 8A:
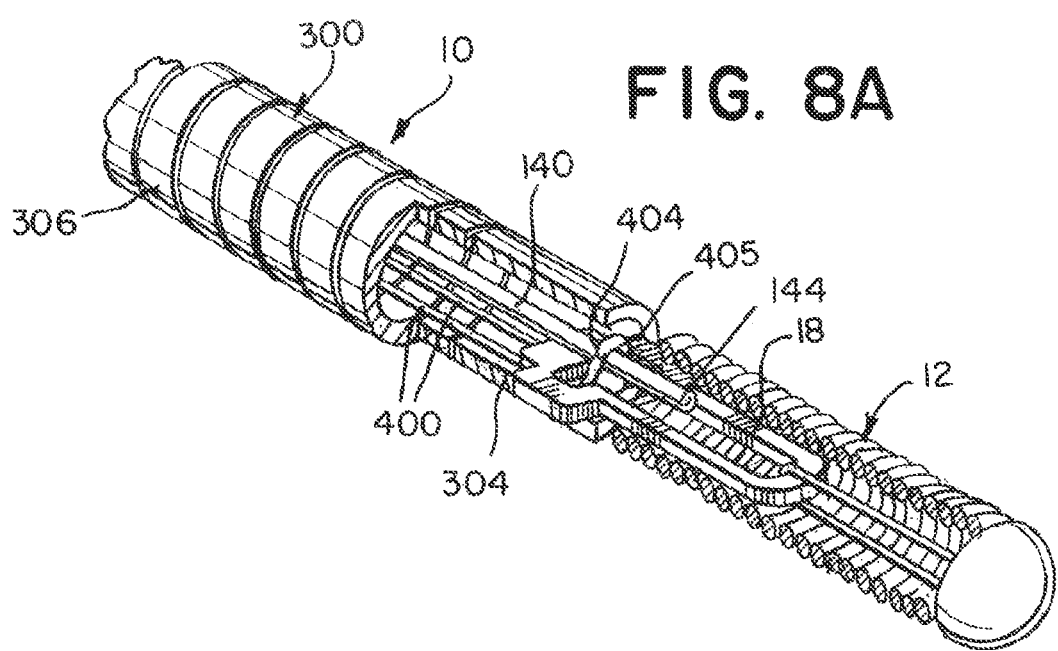
FIGS. 8A-8D illustrate a sequence of steps for releasing an implant from the delivery system, according to aspects of the present invention.
Figure 8B:
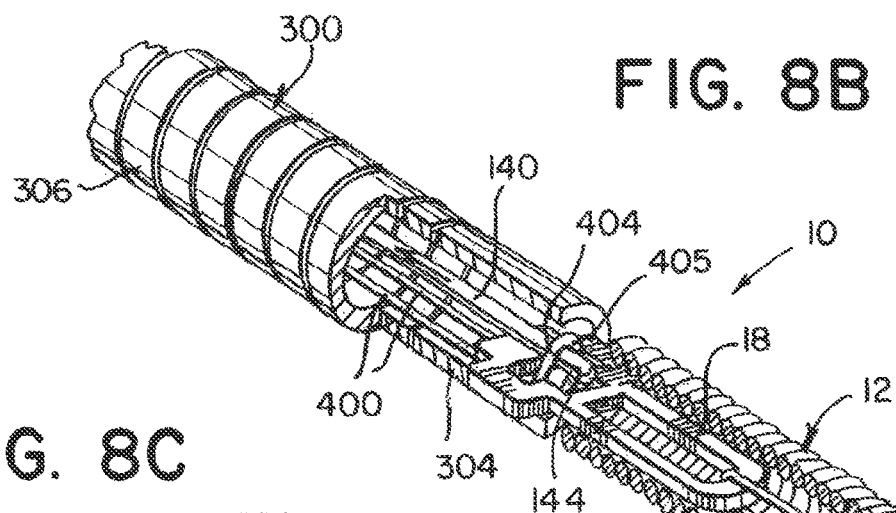
Figure 8C:
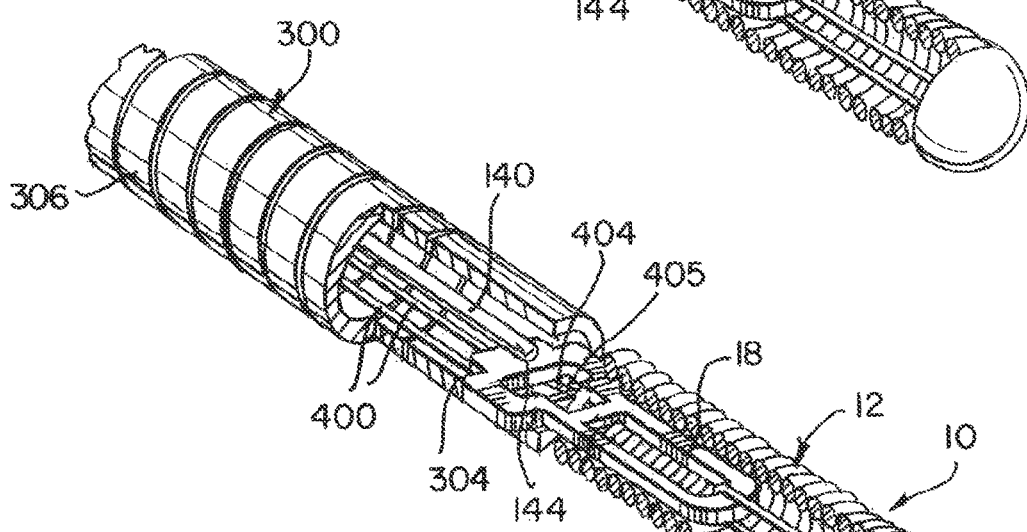
Figure 8D:
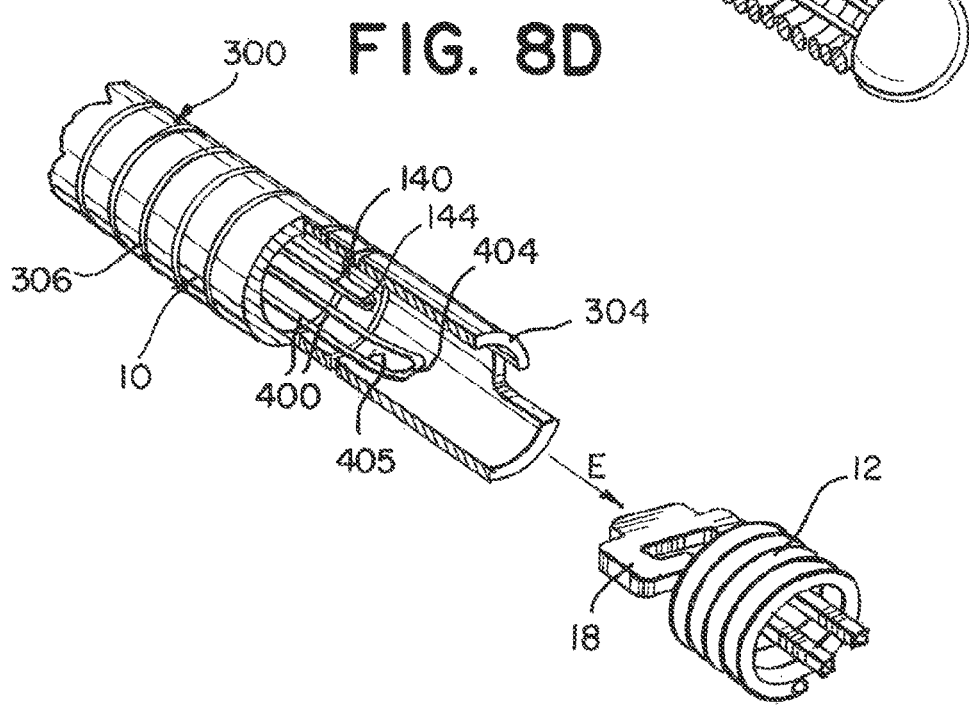

FIGS. 8A-8D illustrate a time sequence of steps for releasing an embolic implant 12 from a delivery system 10. The delivery system 10 and implant 12 can be configured such as illustrated in the previous figures and as otherwise described herein. FIG. 8A illustrates an engagement system including the loop wire 400 and pull wire 140 locked into a locking portion 18 of the medical device 12, thereby forming a sub-assembly. The spiral cuts 306 of the compressible distal portion 300 can be compressed and the loop wire 400 opening 405 at a distal end 404 of the loop wire 400 can be placed through the locking portion 18. When the pull wire 140 is put through the opening 405 the medical device 12 is now secure. FIG. 8B illustrates the pull wire 140 being drawn proximally to begin the release sequence for the medical device 12. FIG. 8C illustrates the instant the distal end 144 of the pull wire 140 exits the opening 405 and the pull wire 140 is pulled free of the loop wire 400. The distal end 404 of the loop wire 400 falls away and disengaged from the locking portion 18. As can be seen, there is now nothing holding the implant 12 to the detachment system 10. FIG. 8D illustrates the end of the release sequence. Here, the compressible distal portion 300 has extended/returned to its original shape and "sprung" forward. An elastic force E is imparted by the distal end 304 of the compressible distal portion 300 to the medical device 12 to "push" it away to ensure a clean separation and delivery of the medical device 12.

The compressible distal portion 306 can have a difference in length (distance of compression) when measured in the compressed configuration and the original, uncompressed configuration of about 0.5 mm to about 0.75 mm. Greater elastic force E can be achieved by using a greater distance of compression. The distance of compression can be determined by the sizing of the loop wire 400, the shape of the locking portion 18, and the shape of the distal end 304 of the compressible distal portion 300.

FIG. 9 is a flowchart of an exemplary method 900 of using the deployment handle and delivery system to deploy an implant. In block 904, the method can include providing a tubular body 90 that includes a lumen 608 extending therethrough. In block 908, the method can include extending pull wire 140 through the lumen 608. In block 912, the method can include providing a proximal support tube 110 that disposed within lumen 608. The proximal support tube 110 can include a marked distal section 114 that is covered by the tubular body 90. The marked distal section 114 can be invisible to an operator of the delivery system 10.

In block 916, the method can include engaging a proximal end 142 of the pull wire 140 to the proximal support tube 110. Proximal translation of the proximal support tube 110 can cause the pull 140 to be translated proximally. In block 920, the method can include securing the implantable medical device 12 to the tubular body 90 with the pull wire 140.

In block 924, the method can include delivering the implantable medical device 12 to the target location of the body vessel. While delivering the implantable medical device, the marked distal section n114 can remain covered by the tubular body 90 such that it is not visible to the operator of the delivery system.

In block 928, the method can include translating the proximal support tube 110 proximally to release the implantable medical device 12 from a distal end 94 of the tubular body 90. The marked distal section 114 can be moved proximally out of the lumen 608 such that the marked distal section 114 becomes visible to an operator of the delivery system. The marked distal section can thereby effectively indicate that the implantable medical device 12 has been successfully deployed at the target location of the body vessel.

The descriptions contained herein are examples of embodiments of the invention and are not intended in any way to limit the scope of the invention. As described herein, the invention contemplates many variations and modifications of the implantation system and associated methods, including alternative geometries of system components, alternative materials, additional or alternative method steps, etc. Modifications apparent to those skilled in the pertinent art are intended to be within the scope of the claims which follow.

The invention claimed is:

1. A delivery system for deploying an implantable medical device to a target location of a body vessel, the delivery system comprising:
a handle comprising an aperture, a handle channel, and a handle button;
a tubular body comprising a lumen extending therethrough;
a pull wire extending through the lumen; and
a proximal support tube disposed within the lumen, a distal portion of the proximal support tube comprising a marked distal section covered by the tubular body such that the marked distal section is not visible to an operator of the delivery system, wherein the proximal support tube engages a proximal end of the pull wire such that proximal translation of the proximal support tube causes the pull wire to be translated proximally thereby releasing the implantable medical device from a distal end of the tubular body,
wherein the proximal support tube is inserted into the aperture of the handle, and interacts with the handle button such that proximal movement of the handle button results in proximal translation of the proximal support tube,
wherein at least a proximal portion of a length of the proximal support tube extends through the handle channel,
wherein proximal translation of the proximal support tube and the handle button results in release of the implantable medical device and moves the marked distal section proximally from the lumen of the tubular body into the handle channel so that the marked distal section is visible only when the handle is completely removed from the tubular body and the proximal support tube, and
wherein the handle is completely removed from the tubular body and the proximal support tube after the release of the implantable medical device.

2. The delivery system of claim 1, further comprising:
a loop wire comprising a loop opening at a distal portion of the loop wire positioned approximate the distal end of the tubular body,
wherein the loop wire and the pull wire are positioned to secure the implantable medical device to the delivery system.

3. The delivery system of claim 2, wherein the implantable medical device is deployed in response to proximal translation of the proximal support tube, which causes a distal end of the pull wire to exit the loop opening, which causes the loop wire and the pull wire to disengage the implantable medical device from the delivery system.

4. The delivery system of claim 1, wherein the marked distal section comprises a laser etching visible to the operator of the delivery system upon deployment of the implantable medical device upon complete removal of the handle from the tubular body and proximal support tube.

5. The delivery system of claim 1, wherein the marked distal section comprises an anodized portion of the proximal support tube visible to the operator of the delivery system upon deployment of the implantable medical device upon complete removal of the handle from the tubular body and proximal support tube.

6. The delivery system of claim 1, wherein the marked distal section comprises a printed or dipped portion of the proximal support tube visible to the operator of the delivery system upon deployment of the implantable medical device upon complete removal of the handle from the tubular body and proximal support tube.

7. The delivery system of claim 1, wherein the marked distal section is visibly distinguishable from a remainder of the proximal support tube.

8. The delivery system of claim 1, wherein a remainder of the proximal support tube comprises a first color, and the marked distal section comprises a second color distinguishable from the first color.

9. The delivery system of claim 1, wherein proximal translation of the proximal support tube of between approximately 6 millimeters and approximately 12 millimeters exposes the marked distal section upon complete removal of the handle from the tubular body and proximal support tube.

10. The delivery system of claim 1, wherein proximal translation of the proximal support tube between approximately 6 millimeters and approximately 12 millimeters is effective to deploy the implantable medical device.

11. The delivery system of claim 1, the tubular body further comprising:

a proximal tube;
a flexible tube distal to the proximal tube; and
a distal tube distal to the flexible tube.

12. The delivery system of claim 11, wherein the flexible tube comprises interference cuts.

13. The delivery system of claim 11, wherein:
the distal tube further comprises a compressed distal portion positioned approximate the implantable medical device; and
the compressed distal portion provides an elastic force against the implantable medical device thereby facilitating the release of the implantable medical device from the delivery system.

14. The delivery system of claim 13, wherein the compressed distal portion further comprises a spiral cut portion of the distal tube.

15. A method for using a delivery system to deploy an implantable medical device to a target location of a body vessel, the method comprising:
providing a tubular body comprising a lumen extending therethrough;
extending a pull wire through the lumen;
providing a proximal support tube disposed within the lumen, the proximal support tube comprising a marked distal section covered by the tubular body such that the marked distal section is not visible to an operator of the delivery system;
engaging a proximal end of the pull wire to the proximal support tube such that proximal translation of the proximal support tube causes the pull wire to be translated proximally;
engaging a proximal end of the proximal support tube to a handle via an aperture in the handle;
engaging at least a proximal portion of a length of the proximal support tube with a handle channel in the handle;
securing the implantable medical device to the tubular body with the pull wire;
delivering the implantable medical device to the target location of the body vessel while the marked distal section remains covered by the tubular body;
translating the proximal support tube proximally by proximally moving a handle button on the handle to release the implantable medical device from a distal end of the tubular body, thereby moving the marked distal section proximally out of the lumen into the handle channel so that the marked distal section is visible only when the handle is completely removed from the tubular body and proximal support tube; and
removing the handle completely from the tubular body and proximal support tube after the release of the implantable medical device, thereby exposing the marked distal section.

16. The method of claim 15, wherein the marked distal section comprises a laser etching visible to the operator of the delivery system upon deployment of the implantable medical device and complete removal of the handle from the tubular body and proximal support tube.

17. The method of claim 15, wherein the marked distal section comprises an anodized portion of the proximal support tube visible to the operator of the delivery system upon deployment of the implantable medical device and complete removal of the handle from the tubular body and proximal support tube.

18. The method of claim 15, wherein the marked distal section comprises a printed or dipped portion of the proximal support tube visible to the operator of the delivery system upon deployment of the implantable medical device and complete removal of the handle from the tubular body and proximal support tube.

19. The method of claim 15, wherein a remainder of the proximal support tube comprises a first color, and the marked distal section comprises a second color distinguishable from the first color.

20. The method of claim 15, wherein proximal translation of the proximal support tube of between approximately 6 millimeters and approximately 12 millimeters exposes the marked distal section upon complete removal of the handle from the tubular body and proximal support tube and is effective to deploy the implantable medical device.

* * * * *